US012582578B2

(12) United States Patent
Petersen et al.

(10) Patent No.: US 12,582,578 B2
(45) Date of Patent: Mar. 24, 2026

(54) COMPLIANCE KIT AND SYSTEM

(71) Applicant: INTELLIGENT DEVICES SEZC INC., George Town (KY)

(72) Inventors: Michael Petersen, Ottawa (CA); Allan Wilson, Ottawa (CA); Dean Brotzel, Ottawa (CA)

(73) Assignee: INTELLIGENT DEVICES SEZC INC., George Town (KY)

( * ) Notice: Subject to any disclaimer, the term of this patent is extended or adjusted under 35 U.S.C. 154(b) by 27 days.

(21) Appl. No.: 18/012,062

(22) PCT Filed: Jun. 24, 2021

(86) PCT No.: PCT/CA2021/050866
§ 371 (c)(1),
(2) Date: Dec. 21, 2022

(87) PCT Pub. No.: WO2021/258208
PCT Pub. Date: Dec. 30, 2021

(65) Prior Publication Data
US 2023/0240944 A1     Aug. 3, 2023

(30) Foreign Application Priority Data
Jun. 24, 2020    (CA) ................................ CA 3084744

(51) Int. Cl.
| | |
|---|---|
| *A61J 1/18* | (2023.01) |
| *A61J 7/04* | (2006.01) |
| *G16H 20/13* | (2018.01) |

(52) U.S. Cl.
CPC .............. *A61J 7/0436* (2015.05); *A61J 1/18* (2013.01); *G16H 20/13* (2018.01); *A61J 2200/30* (2013.01); *A61J 2205/60* (2013.01)

(58) Field of Classification Search
CPC .......... A61J 7/0436; A61J 7/04; A61J 7/0454; A61J 7/0084; A61J 7/0076
See application file for complete search history.

(56) References Cited

U.S. PATENT DOCUMENTS

| | | |
|---|---|---|
| 6,244,462 B1 | 6/2001 | Ehrensvard et al. |
| 6,616,035 B2 | 9/2003 | Ehrensvard et al. |
| (Continued) | | |

FOREIGN PATENT DOCUMENTS

| | | |
|---|---|---|
| CA | 2353350 A1 | 1/2003 |
| WO | 2009135283 A1 | 11/2009 |
| (Continued) | | |

OTHER PUBLICATIONS

International Search Report and Written Opinion for International Application No. PCT/CA2021/050866 dated Aug. 9, 2021.
(Continued)

*Primary Examiner* — Benyam Haile
(74) *Attorney, Agent, or Firm* — Fitch, Even, Tabin & Flannery LLP

(57) ABSTRACT

There is provided a compliance system and kit for patient compliance over an extended period of time and/or for higher numbers of doses. In one embodiment, several dosage packages are physically connected together to make a kit. Such an arrangement ensures a specific dose taking order across the packages so a patient cannot take doses out of order. There is provided a compliance kit comprising: multiple smart packages in a connected kit, each smart package containing a tag for monitoring each medication dose removed by a user; at least one reader configured to read a signal from each tag of each smart package; and a CPU for receiving data from the at least one reader, the data representing the signal from each tag.

16 Claims, 6 Drawing Sheets

(56) References Cited

U.S. PATENT DOCUMENTS

| | | | |
|---|---|---|---|
| 6,628,199 | B1 | 9/2003 | Ehrensvard et al. |
| 7,113,101 | B2 | 9/2006 | Petersen et al. |
| 7,170,409 | B2 | 1/2007 | Ehrensvard et al. |
| 7,178,417 | B2 | 2/2007 | Petersen et al. |
| 7,616,116 | B2 | 11/2009 | Ehrensvard et al. |
| 7,772,974 | B2 | 8/2010 | Ehrensvard et al. |
| 2003/0099158 | A1* | 5/2003 | De la Huerga ....... A61J 1/1437<br>368/10 |
| 2007/0278285 | A1 | 12/2007 | Ehrensvard et al. |
| 2008/0053222 | A1 | 3/2008 | Ehrensvard et al. |
| 2008/0191174 | A1 | 8/2008 | Ehrensvard et al. |
| 2013/0304255 | A1* | 11/2013 | Ratnakar ............. G07F 17/0092<br>700/242 |
| 2017/0351838 | A1* | 12/2017 | Chen ...................... G16H 20/10 |
| 2021/0280285 | A1* | 9/2021 | Javitt ..................... G16H 10/60 |
| 2022/0342972 | A1* | 10/2022 | Van Os ................ G06V 40/172 |

FOREIGN PATENT DOCUMENTS

| | | | |
|---|---|---|---|
| WO | 2013159198 | A1 | 10/2013 |
| WO | 2017/176571 | A1 | 12/2017 |
| WO | 2016196140 | A1 | 12/2021 |

OTHER PUBLICATIONS

Supplemental Search Report and Opinion, EP21828792, Oct. 18, 2023.

* cited by examiner

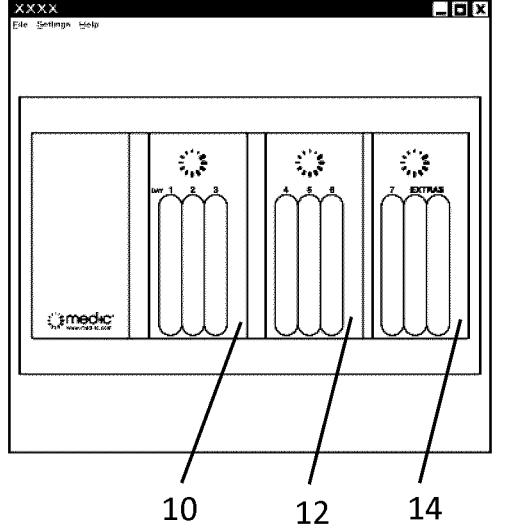
FIG. 1.0
10          12          14
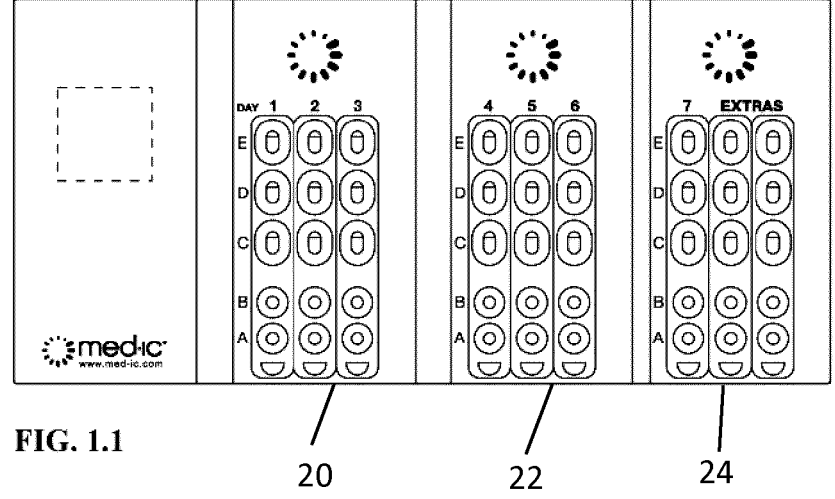
FIG. 1.1
20          22          24

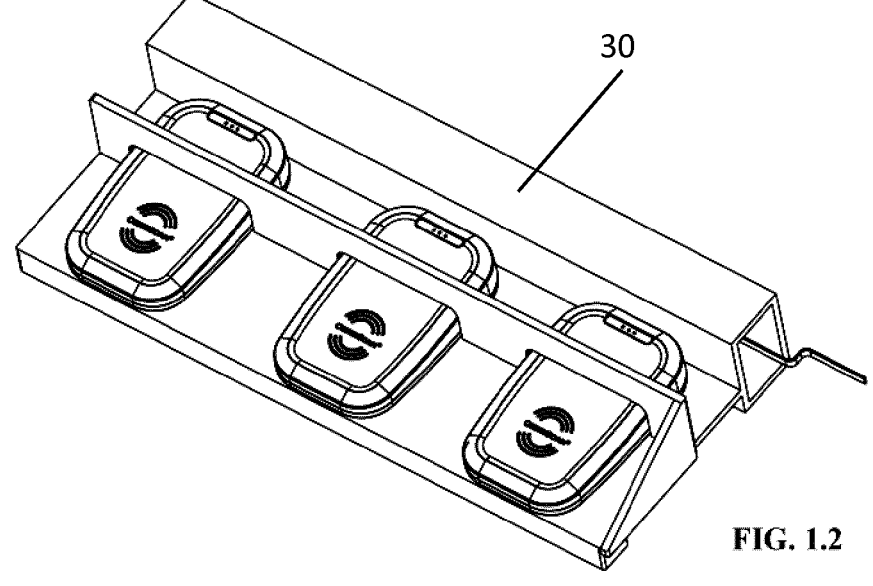
30
FIG. 1.2
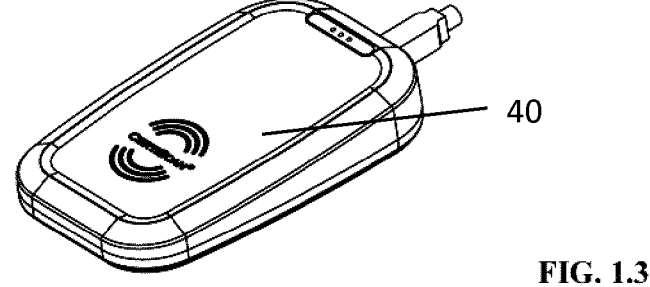
40
FIG. 1.3

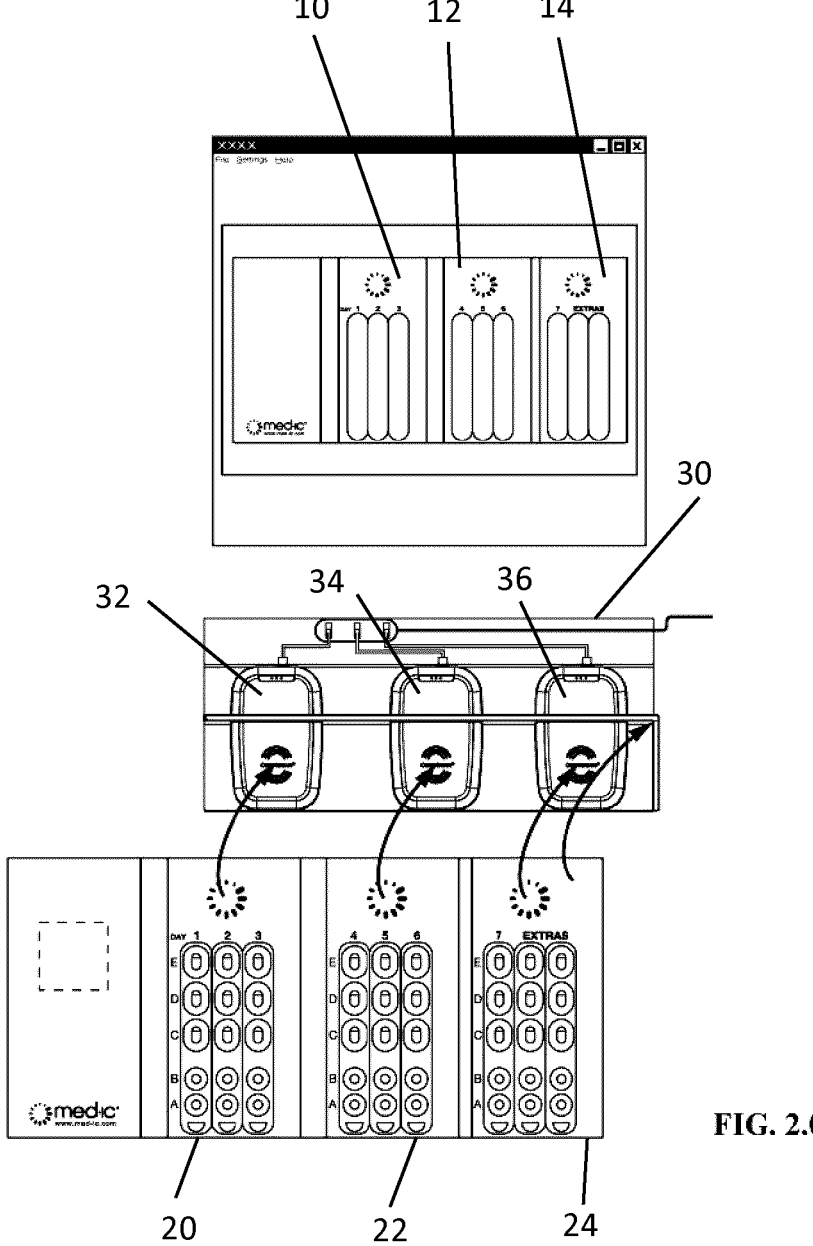
FIG. 2.0

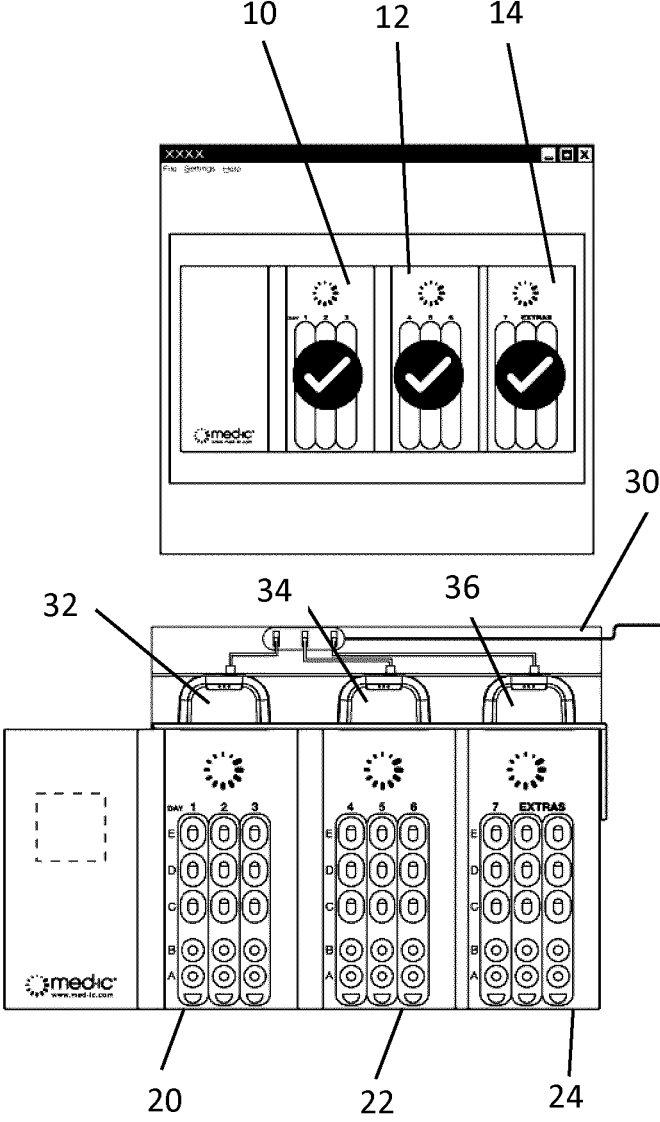
FIG. 2.1

10    12    14
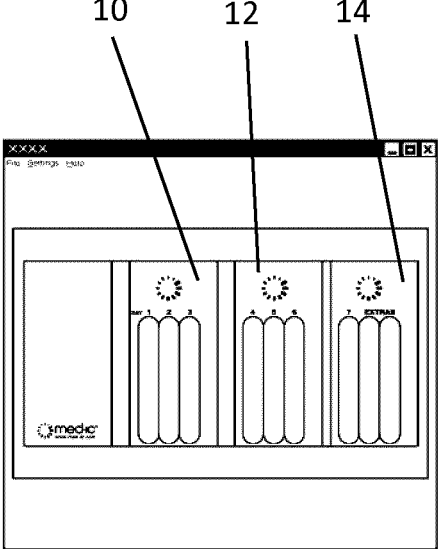
40
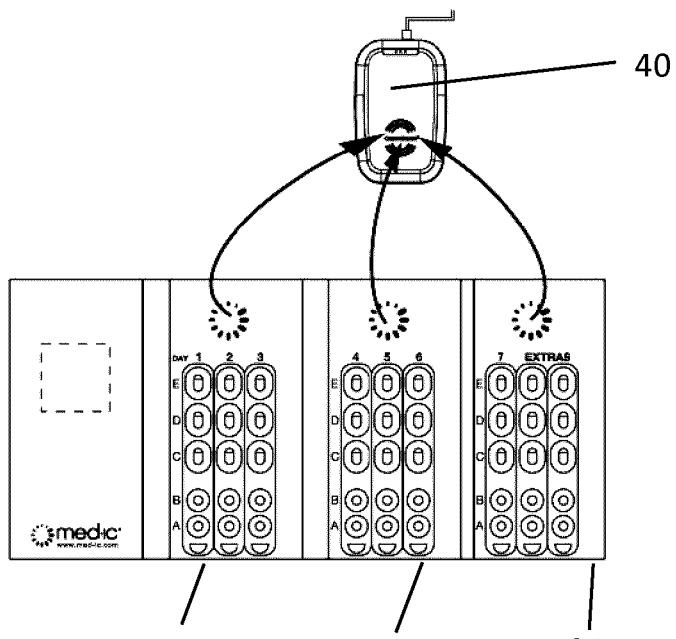
20    22    24
FIG. 3.0

10          12          14
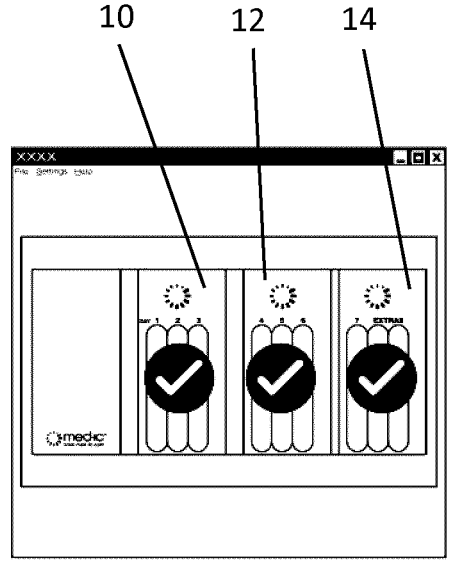
40
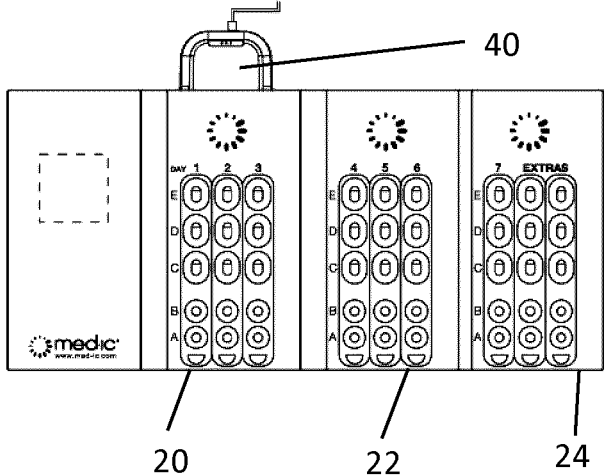
20          22          24
FIG. 3.1

COMPLIANCE KIT AND SYSTEM

CROSS-REFERENCE TO RELATED APPLICATIONS

This application is a United States national phase application filed under 35 U.S.C. § 371 of International Application PCT/CA2021/050866, filed Jun. 24, 2021, designating the United States, which claims priority from Canadian Patent Application Number 3084744, filed Jun. 24, 2020.

TECHNICAL FIELD

The present invention relates to a kit for patient compliance over an extended period of time.

BACKGROUND

Devices for monitoring, recording and downloading medication compliance data for vials, bottles, syringes and blister packages are well known. Allan Wilson, Michael Petersen, Dean Brotzel, Jakob Ehrensvaerd and Stina Grip, amongst others, have described such devices for blister packaged medication, for example U.S. Pat. Nos. 7,113,101, 7,178,417, 6,628,199, 6,244,462, 7,170,409, 6,616,035, 7,616,116 and 7,772,974; PCT applications WO/2009/135283, and WO 2013/159198 A1 Canadian application No. 2353350 and US Publication Nos. 20070278285, 20080191174 and 20080053222. Such devices are commonly referred to as smart packages.

Encouraging patients to adhere to medication dosage regimes can be difficult, yet further ensuring that the medication dosage regimes are followed can be critical. Many patients take several medications each day, each medication having a different dosage regime and requiring different quantities. Furthermore, each medication often has dosage requirements, timing requirements, food intake requirements and other related elements, which can be difficult for a user to track.

Often patients receive medication packaged in separate packages for each week. A patient could then receive a supply of five packages for a month. In such an instance, the patient generally uses the packages in any order. Each month a patient will need to renew their prescription or pick up a new set of packages for the next month.

Sometimes it is necessary, however, to change the dosage throughout the month or to ensure a patient consumes the doses in a particular order. Other times it is necessary to ensure patient compliance throughout the month. While it is known to provide individual smart packages that are prepared for a short period of time or small number of doses, there is needed a system for monitoring compliance over longer periods of time or for higher numbers of doses.

Connecting a large number of doses to a single smart tag becomes difficult due to the complexity of printed sensor circuits. A smart package containing a tag is typically limited to only 23 connections. Some packages, particularly in clinical trials require more doses, such as 45, or even 90.

SUMMARY

There is provided herein a connected kit for monitoring compliance over longer periods of time and/or for higher numbers of doses. In one embodiment, several dosage packages are physically connected together to make a kit. Such an arrangement ensures a specific dose taking order across the packages so a patient cannot take doses out of order. Such an arrangement also enables multiple doses, such as 46, 69 or more or variations thereof.

In one aspect, the system handles multi-tag packages referred to as "connected kits" and includes software that has special features to handle the multiplicity of tags. Thus, the software determines that a scanned tag belongs to a connected kit and prompts/waits for the remaining tag(s) to be scanned so the complete connected kit has been transferred to the database. The software further is able to decipher and determine which information came from which tag. Information is then displayed on a screen for a user.

In a further embodiment, there is provided a connected kit comprising several packages so that several events can be detected with multiple tags and grids. In this fashion, a single tag can detect 23 doses of one type, for example, thus multiple tags can be used to detect larger dose packages and/or multiple types of doses or medication.

In one example embodiment, the connected kit can be used to build complex packages from a single tag design, having common case requirements and able to record 23 doses at a maximum, for example. For packages requiring greater dose count detection, multiple tags and sensors can be used. Such a design has several benefits, such as reducing the variations between types of smart packages or devices, thereby requiring less designs and inventory for devices. In addition, the kit avoids the necessity of designing and building a "super" tag that can detect many doses for testing or other routine procedures since such a tag would hardly be used and would be expensive. Similarly, the kit avoids the necessity of designing a large grid to detect many doses for a "super" tag since any such grid would be very expensive and difficult to manufacture.

The production of a connected kit is not as simple as connecting multiple packages together. In one embodiment, unique metadata is used on each of the tags within a connected kit in order to determine which tag detected an event.

BRIEF DESCRIPTION OF THE DRAWINGS

The invention will be further understood from the following description with reference to the attached drawings.

FIG. 1.0 shows a sample software displaying results of the compliance data received from a connected kit.

FIG. 1.1 shows a sample connected kit containing three smart packages.

FIG. 1.2 depicts a sample set of DTRs (Data Terminal Readers) as part of a toolkit jig or multi-reader jig connected to a CPU or computer (not shown) for use at a production site.

FIG. 1.3 depicts a sample single DTR for connection to a CPU or computer (not shown) for use at a clinical site.

FIG. 2.0 depicts a sample connection at a production site where the package is aligned according to the toolkit jig from FIG. 1.2 which shows three readers that are connected to a USB hub, which is then connected to the CPU software.

FIG. 2.1 depicts an example of the software display containing checkmarks and illustrating each of the tags for each of the smart packages that have been read.

FIG. 3.0 depicts an example of a single DTR scanning each of the tags from each of the smart packages.

FIG. 3.1 depicts an example of the software display containing checkmarks and illustrating each of the tags for each of the smart packages that have been read after the scans performed in FIG. 3.0.

DETAILED DESCRIPTION OF PREFERRED EMBODIMENTS

The exemplary embodiments of the present disclosure are described and illustrated below to encompass a dynamic display and compliance system for example purposes only. It will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

In one aspect involving manufacture or production, there is provided a connected kit comprising several packages so that several events can be detected with multiple tags and grids. A multi reader jig setup and software are used to ensure the correct tags receive the correct metadata based on position. The metadata allows systems downstream to gather and organize information so the information can be displayed as if the data is coming from one normal large package.

In one aspect involving use at a clinical site, multi reader jigs are not possible to use, thus there is provided a different solution in which each tag is scanned one at a time and metadata on the tags are used to put the information together so the information can be displayed as if the data is coming from one normal large package.

The drawings highlight two specific scenarios: (1) manufacture and (2) use at the clinical sites.

FIG. 1.0 shows a sample software displaying results of the compliance data received from a connected kit. Such a set up could be used at both a production site and/or a clinical site. The three sets of information 10, 12, 14 provide the results from three packages in a connected kit.

In an example embodiment, FIG. 1.1 shows a sample connected kit containing three smart packages 20, 22, 24. The metadata on the tags on the smart packages 20, 22, 24 are used to put the information together in FIG. 1.0 so the information 10, 12, 14, coming from smart packages 20, 22, 24 is displayed as if the data is coming from one normal large package.

In a further example embodiment, FIG. 1.2 shows a sample set of DTRs (Data Terminal Readers) as part of a toolkit jig or multi-reader jig 30 connected to a CPU or computer (not shown) for use at a production site. This multi-reader setup provides the ability to ensure the correct tags receive the correct metadata based on position.

FIG. 1.3 illustrates an example sample single DTR 40 for connection to a CPU or computer (not shown) for use at a clinical site.

Stemming from FIG. 1.2, FIG. 2.0 shows an example embodiment at a production site wherein a connected kit containing three smart packages 20, 22, 24 is connected to a toolkit jig or multi-reader jig 30 using three DTRs 32, 34, 36. The three DTRs 32, 34, 36 are connected to a USB hub and then connected to CPU or computer software. The smart package is aligned according to the toolkit jig 30 from FIG. 1.2 As shown in FIG. 1.0, the three sets of information 10, 12, 14 provide the results from three smart packages 20, 22, 24 in the connected kit.

FIG. 2.1 shows an example embodiment of the software display containing checkmarks which illustrate that each of the tags for each of the smart packages 20, 22, 24 have been read. The DTRs 32, 34, 36 are shown reading the data from each of the respective smart packages 20, 22, 24. The software can then provide the results and information for each smart package on the display screen. In this embodiment the toolkit jig or multi-reader jig 30 from FIG. 2.0 scans all three tags either sequentially or simultaneously and then provides the scanned results to the software. The three sets of information 10, 12, 14 provide the results from three smart packages 20, 22, 24 in the connected kit. Such an arrangement can be used at a production site.

Stemming from FIG. 1.3, FIG. 3.0 shows an example embodiment involving a single DTR 40 scanning each of the tags from each of the smart packages 20, 22, 24 simultaneously or sequentially, one at a time. The reader, i.e. DTR 40, then provides the scanned results to the software. Such an arrangement can be used at a nurse or client site. The three sets of information 10, 12, 14 provide the results from three smart packages 20, 22, 24 in the connected kit.

FIG. 3.1 shows an example embodiment of the software display containing checkmarks which illustrate that each of the tags for each of the smart packages 20, 22, 24 have been read after the scans performed in FIG. 3.0. When the scans are performed sequentially, after each of the scans, the software displays the results. The three sets of information 10, 12, 14 provide the results from three smart packages 20, 22, 24 in the connected kit.

In yet a further example embodiment, the tags on each smart package include a proprietary command set beyond standard NFC to allow scanning of multiple tags placed over a reader simultaneously. In this manner, the tags of the smart readers in FIGS. 3.0 and 3.1 can be scanned at the same time with a single reader. In one example in order to scan such tags simultaneously, the smart packages can be folded to align the tags on each smart package.

In one example, the metadata can be a code specifically identifying the tag (e.g. 2021-10-22-12345). The metadata can include date of manufacture or other information to uniquely identify the tag. The metadata can further include a sequence to identify the order of the tag within the connected kit (e.g. 1-2021-10-22-12345, 2-2021-11-01-78910). In the foregoing example, the format of the metadata is as follows "number of tag in connected kit"–"date of manufacture"–"tag id". Other forms of metadata can also be used containing other identity information for the tag. A CPU can stitch the data together from the kit based on the received "number of tag in connected kit" from the metadata for each tag, such that even if the scanned data/information from the tags is not received by the CPU in order, the CPU can reorder the scanned data/information based on the metadata and the order of the tag in the kit. This will permit the CPU to present the data to the user in an order that matches the order of the tags in the connected kit. As will be appreciated, the identity of the tag in the connected kit does not need to be represented by a number in the metadata. It can be represented through letters, binary symbols or any other manner of identification.

The present invention provides many advantages. For example, it is more advantageous to have multiple smaller grids rather than one large dose grid due to reduced cost which is provided as a result of lower yields and volume on each smaller grid. Furthermore, for complex designs the present invention enables the user to include multiple specialized grids rather than attempting to create a large generic grid to include each blister package design. Such a large generic grid can cause many complications when trying to avoid the grid having to cross a folding spine.

It will be appreciated by one skilled in the art that variants can exist in the above-described arrangements and applications. For example, the tools provided for use at a production site can be used at any other type of site depending upon the needs of the user, such as a nurse site or client site. As a further example, individual smart packages might be connected together within a container or other compartment rather than connected directly to each other. As another example, connected blister cards/smart packages can be connected together and folded into a z-fold package. As a further variation, the computer or CPU can take any form, such as a desktop computer, mobile phone, laptop, tablet, smart watch, etc. The communication from the reader or DTR to the CPU can occur through either wired or wireless communication.

While the foregoing discussion and example embodiments have been illustrated with the use of three smart packages, three DTRs and three sets of information shown on a display, it will be appreciated that the number of smart packages in the connected kit can be more or less than three and can include any number of smart packages as required or desired.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Consequently, the scope of the claims should not be limited by the preferred embodiments set forth in the examples but should be given the broadest interpretation consistent with the description as a whole. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A compliance kit comprising:
a connected kit formed from multiple smart packages connected together and organized in an order, each smart package configured to securely contain at least one medication dose and containing a tag for monitoring each medication dose removed by a user from each smart package;
at least one external tag reader configured to read a signal from each tag of each smart package, the at least one external tag reader separate from the connected kit; and
a CPU for receiving data from the at least one external tag reader, the data representing the signal from each tag;
wherein the data includes metadata containing identity information for each tag, and the CPU is configured to use the metadata to determine which of the tags provided the data, to reorder the received data based on the metadata, and to present the data to a user in a specific order that matches the order of the tags in the smart packages in the connected kit.

2. The compliance kit of claim 1, wherein the data contains information pertaining to time, quality and/or quantity of medication removed by a user.

3. The compliance kit of claim 2 further comprising a display controllable by the CPU, wherein the display is configured to display information pertaining to the data in the order of the tags.

4. The compliance kit of claim 3 wherein the at least one external tag reader reads the signal from each tag of each smart package and the information is displayed on the display in real-time after each tag is read.

5. The compliance kit of claim 4 wherein the at least one external tag readers comprises a plurality of tag readers that are part of a toolkit jig connected to a USB hub.

6. The compliance kit of claim 5, wherein the toolkit jig is configured to ensure the correct tags receive the correct metadata based on position during setup of the connected kit.

7. The compliance kit of claim 3 wherein the display provides an indication once each smart package has been read.

8. The compliance kit of claim 3 wherein the CPU is configured to use the metadata to present the information on the display in an order that matches an order of the smart packages.

9. The compliance kit of claim 3 wherein the CPU is configured to send a read-status to the display to confirm when each said tag of each smart package has been read by said at least one reader.

10. The compliance kit of claim 3 wherein the CPU is configured to use the metadata to arrange the display information in an order that matches the order of the smart packages.

11. The compliance kit of claim 3 wherein the CPU is configured to provide the information for each smart package on the display and the display is configured to illustrate that each of the tags for each of the smart packages have been read.

12. The compliance kit of claim 1 wherein the at least one external tag reader includes multiple readers, wherein the multiple readers include a reader for each smart package and the multiple readers are configured to receive the signal from each tag of each smart package simultaneously.

13. The compliance kit of claim 1 wherein the at least one external tag reader reads the signal from each tag of each smart package simultaneously.

14. The compliance kit of claim 1 wherein the at least one external tag reader reads the signal from each tag of each smart package individually.

15. The compliance kit of claim 1 wherein the CPU receives the data from the at least one external tag reader and determines which of the tags provided the data based on position of the tag in the connected kit.

16. The compliance kit of claim 1, wherein the CPU is configured to determine that a scanned tag belongs to the kit and to prompt or wait for all of the tags to be scanned so the data from all of the tags is transferred to a database.

* * * * *